(12) United States Patent
Blount et al.

(10) Patent No.: US 6,399,052 B2
(45) Date of Patent: Jun. 4, 2002

(54) TREATING HAIR BY TARGETING ENZYMES

(75) Inventors: Margaret Ann Blount; Michael Arthur Davis, both of Bedford; Kelly Jackson, Bebington; Nathalie Noel, Bebington; Matthew Leslie Pearce, Bebington; Paul Slusarewicz, Bedford, all of (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/878,652

(22) Filed: Jun. 11, 2001

Related U.S. Application Data

(62) Division of application No. 09/533,634, filed on Apr. 20, 2000, now abandoned.

(30) Foreign Application Priority Data

Apr. 22, 1999 (GB) ............................................. 9909294.2

(51) Int. Cl.$^7$ ........................... A61K 7/09; A61K 31/38; A01N 55/02; A01N 43/02
(52) U.S. Cl. ........................ 424/70.5; 514/185; 514/430
(58) Field of Search .................. 424/70.1, 94.1, 424/70.5; 435/183; 514/185, 430

(56) References Cited

U.S. PATENT DOCUMENTS

| | | | |
|---|---|---|---|
| 4,192,861 A | 3/1980 | Micchelli et al. | 424/47 |
| 4,851,214 A | 7/1989 | Walters et al. | 424/65 |
| 5,143,925 A | 9/1992 | Shander et al. | 514/378 |
| 5,490,980 A | 2/1996 | Richardson et al. | 424/94.6 |
| 5,525,336 A | 6/1996 | Green et al. | 424/94.5 |
| 5,614,180 A | 3/1997 | Chung | 424/70.19 |
| 5,633,151 A | 5/1997 | McNeill | 435/134 |
| 5,705,147 A | 1/1998 | Shapiro et al. | 424/70.1 |

FOREIGN PATENT DOCUMENTS

| | | |
|---|---|---|
| DE | 42 02 645 | 6/1993 |
| DE | 198 24 073 | 12/1999 |
| EP | 0116439 | 2/1984 |
| EP | 0117087 A | 8/1984 |
| EP | 0562637 | 9/1993 |
| FR | 2706769 | 12/1994 |
| FR | 2734477 | 11/1996 |
| FR | 2740331 A | 4/1997 |
| GB | 2140297 A | 11/1984 |
| GB | 2261818 | 6/1993 |
| WO | 99/36570 | 7/1999 |
| WO | 99/37279 | 7/1999 |

OTHER PUBLICATIONS

International Search Report Application No. PCT/EP 00/03078 mailed Jan. 5, 2001.
Derwent Publications Ltd. London, GB; Class A96, AN 1992–138620—XP002144347 & JP 04 082817 A to Saruno.
Patent Abstracts of Japan vol. 011, No. 353 (C–457), & JP 62 126110 A to Kanebo Ltd.
Patent Abstracts of Japan vol. 1999. No. 01, & JP 10 279437 A to Shiseido Co., Ltd.
Patent Abstracts of Japan, vol. 1999, No. 13, & JP 11228352 A to Kanebo, Ltd.
Patent Abstracts of Japan, vol. 014, No. 535 (C–0781) & JP 02 223529 A to Taisho Pharmaceut. Co. Ltd.
Derwent Publications Ltd. London, GB; Class B04, AN 1992–263010 XP 002153187 & JP 04 178335 to Taiyo Kagaku KK.
Okamoto, K.: "Studies on the Quantity and Chemical Composition of Surface Lipids of Human Scalp and Hair", The Journal of Dermatology, vol. 7, No. 2, XP000960901.
Favre, Anna: "The Enzymes of the Skin, I. Esterase Activity" Relata Tech., vol. 15, No. 36, XP 000960902.
Database Caplus, AN 1977: 451337, Kass: "Nonspecific Esterase Activity in 'Hairy Cells'" XP 002153186 Abstract & Acta Haematol.

*Primary Examiner*—Christopher R. Tate
*Assistant Examiner*—Mike Meller
(74) *Attorney, Agent, or Firm*—Matthew Boxer

(57) ABSTRACT

The invention provides the use of a hair benefit agent as an ingredient in a topical hair treatment composition for the purpose of targeting an active endogenous hair fiber enzyme when the composition is applied to the hair, thereby delivering a hair benefit via the interaction of the hair benefit agent with the enzyme.

1 Claim, No Drawings

TREATING HAIR BY TARGETING ENZYMES

This is a divisional of Ser. No. 09/553,634 filed Apr. 20, 2000, now abandoned.

FIELD OF THE INVENTION

This invention relates to the treatment of hair with activators, inhibitors, co-factors or catalytic substrates for active endogenous hair fibre enzymes.

BACKGROUND AND PRIOR ART

The vast number of biochemical reactions that occur in every human cell are nearly all mediated by enzymes. Enzymes are biological catalysts, facilitating reactions under mild and physiological conditions. All enzymes have a defined function and are highly specific for the reactions they catalyse. A particular enzyme could therefore be targeted by a specific reagent, whilst other enzymes remain unaffected. In addition, the types of reactions catalysed by different enzymes is extremely variable, and each enzyme is capable of catalysing up to a million reaction events per second.

Enzymes are of particular interest for the development of new modes of benefit delivery in hair care. For example, U.S. Pat. No. 5,490,980 describes a composition for topical application to skin, hair or nails containing a beneficial active agent which has been functionalised with an alkylamine moiety, together with the enzyme transglutaminase (a calcium and thiol dependent enzyme responsible for the crosslinking of proteins by the formation of covalent bonds between lysine and glutamine residues). The transglutaminase in the composition is said to act as a catalyst to crosslink the active ingredient with glutamine residues in skin, hair or nails. The transglutaminase in the composition of U.S. Pat. No. 5,490,980 is sourced from guinea pig liver, slime mould, alfalfa or preferably bacterial fermentation.

Problems with the above approach include size exclusion of the exogenous enzyme, the expense of obtaining the exogenous enzyme, the possibility of immunological sensitisation from enzyme-containing formulations, and instability of the enzyme when stored in the formulation, particularly where high surfactant levels are present as in cleansing compositions. Furthermore, Gardner et al. (1995) J. Soc. Cosmet. Chem., 46, 11–28 provides evidence that glutamine residues on the surface of human hair are not, contrary to previous thought, recognised as a substrate for guinea pig liver transglutaminase. The authors of that paper found no conclusive evidence that virgin hair was modified by exogenously applied transglutaminase, and considered that the outer fatty acid layer of the hair probably restricted access to candidate glutamine sites, despite the large abundance of glutamine residues in hair, through hydrophobic repulsion or steric interactions. It was suggested that future work should be directed to cross-linking soluble protein or modified protein films co-deposited on hair together with the exogenous enzyme, so that the hair was not required to donate endogenous residues to the reaction.

Tsushima et al., Arch. Dermatol. Res. 284: 380–385 (1992) describes the purification and characterisation of a cystatin-type cysteine proteinase inhibitor (CPI) in the human hair shaft. In that paper, it is speculated that there are cysteine proteinases in hair, since there is CPI. However, the presence of any such enzymes within the hair fibre has, to date, not been reported in the literature.

The inventors have now found that the mature human hair fibre contains endogenous enzymes, which furthermore have been shown to be active and therefore capable of interaction with exogenously supplied substrates. The precise origin of these active endogenous hair fibre enzymes remains unclear. It is particularly surprising that these endogenous hair fibre enzymes have not only been shown by the inventors to be present, but also to be biologically active. Maturation of hair fibre results in the death of its constituent cells (Tamada et al. (1994) Br. J. Dermatol. 131: 521–524) and this coupled with the increased levels of intracellular cross-linking results in a mature fibre which is metabolically dead. Unexpectedly, the inventors have found that enzyme activity is in fact preserved, rather than denatured, during the processes of cellular keratinisation and death that occur during fibre growth.

SUMMARY OF THE INVENTION

The present invention provides the use of a hair benefit agent as an ingredient in a topical hair treatment composition for the purpose of targeting an active endogenous hair fibre enzyme when the composition is applied to the hair, thereby delivering a hair benefit via the interaction of the hair benefit agent with the enzyme.

Advantageously, the above approach solves the problems associated with the systems described previously involving application of exogenous enzyme. For example, enzyme substrates can be selected which are cheaper, safer and stabler to formulate into hair treatment compositions than exogenous enzyme, and which, unlike exogenous enzyme, are able to penetrate the hair and actually deliver enzyme-linked benefits to the underlying fibre matrix.

DETAILED DESCRIPTION AND PREFERRED EMBODIMENTS

Examples of active endogenous enzymes identified by the inventors to date within the mature human hair fibre fall in various and diverse classes and include:

Transglutaminase
Protease
Lipase
Steroid sulphatase
Catalase
Esterase

Hair Benefit Agents

Ingredients suitable for use as hair benefit agents according to the invention for targeting endogenous hair fibre enzymes may be any material which is capable of specifically interacting with the selected enzyme, or is chemically modified in order to do so. The material may serve as an enzyme activator, enzyme inhibitor, enzyme co-factor or catalytic substrate for the enzyme, in order to derive benefit.

Examples of the type of such ingredients include hair conditioning agents, (such as humectants, softeners and cuticle lubricants), hair colouring agents, antimicrobial compounds, UV-absorbing compounds, fluorescers, hair strengthening agents (such as fibre repair agents or fibre rebuilding agents), antioxidants, perfumes, and mixtures thereof.

Preferred ingredients for use according to the invention are selected to target the endogenous hair fibre enzymes which are classified below:

(i) Transglutaminase

Transglutaminase has been found to be active in the hair fibre, localised predominantly in the cuticle. It is a calcium and thiol dependent enzyme which is responsible for the crosslinking of proteins by the formation of covalent bonds between lysine and glutamine residues.

Ingredients suitable for use as hair benefit agents according to the invention for targeting endogenous hair fibre transglutaminase include catalytic substrates for this class of enzyme.

Catalytic substrates for transglutaminase are required to include (or be modified to include) at least one —R'NH$_2$ group in which R' is a hydrocarbon or functionalised hydrocarbon chain. Preferably R' is a straight aliphatic hydrocarbon chain containing from 1 to 8 carbon atoms.

Transglutaminase crosslinks the substrate through the alkyl amine (R'NH$_2$) group to the glutamine residues in hair.

Accordingly, hair benefit agents suitable for use according to the invention as catalytic substrates for endogenous hair transglutaminase may be any compound which has a beneficial effect when delivered to human hair, as long as the compound contains, or is modified to contain, an alkyl amine group.

Use of such hair benefit agents as catalytic substrates for endogenous hair fibre transglutaminase enables a direct, in situ interaction between substrate and enzyme for delivering a localised and sustained hair fibre benefit derived from that interaction. In this way, permanent or internal hair benefits may be obtained from the transglutaminase-catalysed crosslinking reaction between a benefit agent and the substance of the hair fibre itself. Preferred benefit agents in this context are hair conditioning agents and hair colouring agents. Advantageously, such enzyme-catalysed interactions occur under physiological and naturally mild reaction conditions, so harsh chemical treatments are not necessary.

Preferably, in order to optimise the crosslinking reaction between transglutaminase and substrate, the R'NH$_2$ group contains at least 4 unbranched carbon atoms adjacent to the NH$_2$ group. Optimal transglutaminase activity is generally achieved when the substrate has (a) alkylamine side-chain lengths equivalent to 5 methylene groups (or 7.2–7.6 Å long), (b) no branching nor groups bulkier than methylene along the alkyl amine chain, (c) hydrophobic moieties attached to the alkyl chain, and (d) more than one alkyl amine group. However, this is not particularly critical and other hydrocarbon chains can be used, (including those incorporating functional groups such as ester, ether or amide linkages or similar), provided the terminal amine group is not sterically hindered from interacting with the active site.

Suitable ingredients which inherently contain an alkyl amine group include intact proteins, protein hydrolysates, chemically modified (e.g. quaternized or acylated) proteins or protein hydrolysates, peptides, non-proteinaceous amino acid polymers (such as amino acid polymers produced by chemical synthesis), amino acids (or derivatives thereof), and primary amine compounds.

Preferred examples include the amino acid lysine, polymers thereof (polylysine) having a molecular weight ranging from 100 to 2,000, and acylated derivatives thereof such as lauroyllysine.

Also preferred are primary amines having a carbon chain of at least $C_{10}$, preferably $C_{12-22}$, such as soya amine, hydrogenated tallow amine, stearyl amine, tallow amine, oleyl amine, hexadecylamine, octadecylamine, and combinations thereof. These materials are preferred since they are capable of imparting smoothness and improved ease of combing to treated hair fibres.

Ingredients may also be used which have a beneficial effect on human hair and which have been modified to contain at least one alkyl amine moiety. U.S. Pat. No. 5,490,980 describes and exemplifies a range of such ingredients and the corresponding process by which they are appropriately modified. Preferred examples are alkyl amine modified silicones which are capable of imparting conditioning benefits to hair.

Activators of endogenous hair fibre transglutaminase may also be used as ingredients according to the invention. Such activators may be used alone, in order to promote fibre strengthening due to enhanced in situ fibre transglutaminase activity, or alternatively in conjunction with one or more of the catalytic substrates described above.

(ii) Protease

Various protease activities have been identified in the hair fibre. These include cysteine and serine proteases, with the major protease observed to date appearing to have similar properties to the lysosomal cysteine proteases, cathepsins L and B. Cathepsins L and B are known to hydrolyse many cytosolic and structural proteins, including collagen and elastin.

Ingredients suitable for use as hair benefit agents according to the invention for targeting endogenous hair fibre protease include inhibitors of this class of enzyme. Examples of such protease inhibitors include cystatins, which are small proteins found widely in nature, for example in eggs and avocado mesocarp. Use of such inhibitors enables reduction or prevention of autohydrolysis of the hair fibre by the active hair fibre protease, thereby protecting against hair fibre damage or deterioration.

Further suitable ingredients for use as hair benefit agents according to the invention for targeting endogenous hair fibre protease are catalytic substrates for protease, i.e. protein, proteinaceous or peptide containing substrates capable of being hydrolysed by the protease into smaller peptides and/or free amino acids.

Examples include collagen, keratin, fibroin, elastin, ovalbumin, casein, gluten, ferritin, gliadin, zein, soy protein, silk protein and hydrolysates or derivatives thereof.

Preferably the substrate is rich in the amino acids lysine, histidine and/or arginine. In this way, hydrolysis of substrate by the enzyme can deliver benefits such as moisturisation to the hair via the release of the free amino acids directly into the hair fibre. For example, preferred protein or proteinaceous substrates contain at least 12%, most preferably at least 15% to about 70% of these amino acids, either singly or in admixture, by weight based on total weight.

Ingredients may also be used which have a beneficial effect on human hair and which have been covalently modified to contain an amino acid or amino acid sequence capable of interacting with endogenous air fibre protease. In this way, protease-mediated catalysis facilitates the gradual release of benefit agent directly into the hair fibre, where it may be allowed to penetrate further into the fibre, without the need for harsh chemical modification processes.

(iii) Lipase

Lipase activity has been found in the hair fibre. Lipases hydrolyse ester linkages in lipids, and in particular those within triacylglycerol. This reaction yields free fatty acids and glycerol. Glycerolipids are the most common substrates that are hydrolysed by the enzyme, although they are relatively non-specific and will also hydrolyse other acyl esters. Lipases are believed to have an important role in hair development where they are involved in the recycling of hair glycerolipids during the formation of cell membrane complex lipids. During hair cell differentiation, the cellular lipids (predominantly glycerolipids) are destroyed and new lipids synthesised such as steroids, ceramides and fatty acids.

Ingredients suitable for use as hair benefit agents according to the invention for targeting endogenous hair fibre lipase include catalytic substrates for this class of enzyme.

Examples are triglyceride fats and oils derived from vegetable, animal and marine sources such as coconut oil, castor oil, safflower oil, cotton seed oil, corn oil, olive oil, cod liver oil, almond oil, avocado oil, palm oil, sesame oil, and soybean oil.

Preferred are triglycerides derived from fatty acids having 8 to 22 carbon atoms. Suitable examples of such fatty acids include pelargonic, lauric, myristic, palmitic, stearic, isostearic, 12-hydroxystearic, oleic, linoleic, ricinoleic, 18-methyleicosanoic, arachidonic, behenic, and erucic acids. In this way, lipase-mediated catalysis facilitates the release of free fatty acids, which are important components of the cell membrane complex, and glycerol, an effective humectant, directly into the hair fibre. Advantageously, targeting of endogenous hair fibre lipase with triglyceride substrates of selected fatty acid content provides a route to influencing the lipid environment of the hair fibre without the necessity for harsh chemical or physical modification processes.

Ingredients may also be used which have a beneficial effect on human hair and which have been covalently tagged with a lipid capable of interacting with endogenous hair fibre lipase.

(iv) Steroid Sulphatase

Steroid sulphatase activity has been identified in the hair fibre. This enzyme catalyses the hydrolysis of cholesterol-3-sulphate into cholesterol (and sulphate). Steroid sulphatase is believed to have an important role in the formation of normal healthy hair, since dramatic hair effects are noticeable in people who are deficient in this enzyme. For example, in patients with X-linked ichthiosis, the enzyme activity is reduced (or non-existent) and the hair feels dry and brittle.

Ingredients suitable for use as hair benefit agents according to the invention for targeting endogenous hair fibre steroid sulphatase include activators of this class of enzyme. Use of such activators enables increased delivery of cholesterol directly into the hair fibre. Cholesterol has been shown to protect hair against damage, enhance hair flexibility and reduce dry feel.

Further suitable ingredients for use as hair benefit agents according to the invention for targeting endogenous hair fibre steroid sulphatase are catalytic substrates for steroid sulphatase such as cholesterol-3-sulphate, which is capable of being hydrolysed by the steroid sulphatase into cholesterol (and sulphate).

(v) Catalase

Catalase activity has been identified in the hair fibre. This enzyme catalyses the conversion of hydrogen peroxide ($H_2O_2$) into water and molecular oxygen.

Ingredients suitable for use as hair benefit agents according to the invention for targeting endogenous hair fibre catalase include activators of this class of enzyme.

Use of such activators provides a route to additional radical damage protection for the hair fibre through increased removal of peroxide. This is particularly advantageous in the case of chemically treated hair (e.g. bleached, coloured or permed) which is especially vulnerable to oxidative damage, and also in climates in which high levels of oxidative stress are encountered.

Use of such activators additionally provides a route to removal of surplus peroxide which is deliberately added to the hair during treatment with products such as bleaches, colorants, and perms in which peroxide is used for the oxidation step. Alternatively, inhibitors of endogenous hair fibre catalase may be used as hair benefit agents according to the invention, as ingredients for increasing the efficacy of peroxide-containing products which are applied to the hair fibre such as colourants, bleaches or perms.

(vi) Esterase

Esterase activity has been identified in the hair fibre. Esterases are a broad class of enzymes that catalyse the hydrolysis of ester linkages.

Ingredients suitable for use as hair benefit agents according to the invention for targeting endogenous hair fibre esterase include catalytic substrates for this class of enzyme.

Catalytic substrates for esterase are required to include (or be modified to include) at least one ester linkage.

Accordingly, hair benefit agents suitable for use according to the invention as catalytic substrates for endogenous hair esterase may be any compound which has a beneficial effect when delivered to human hair, as long as the compound contains, or is modified to contain, an ester linkage.

In this way, benefit agents may be used in esterified form, (for example, conjugated via an ester linkage to an inert carrier molecule), and used to target endogenous hair fibre esterase, so that upon hydrolysis by endogenous hair fibre esterase, the benefit agent is released and thus activated, allowing a controlled release of the benefit agent directly into the hair fibre. This is particularly advantageous in the case of benefit agents which in free (unesterified) form are sensitive to factors such as heat, oxidation, light, moisture, pH, or microbial attack, or which tend to react with other ingredients in a formulation. Examples of such benefit agents include perfumes, colourants, antioxidants such as vitamins A, C and E, and natural hair nutrients such as lipids and amino acids.

Product Form

The final product form of hair treatment compositions according to the invention may suitably be, for example, shampoos, conditioners, sprays, mousses or lotions. Particularly preferred product forms are shampoos, post-wash conditioners (leave-in and rinse-off) and hair treatment products such as hair essences and hair oils.

Shampoo Compositions

A particularly preferred hair treatment composition in accordance with the invention is a shampoo composition.

Cleansing Surfactant

Such a shampoo composition will comprise one or more cleansing surfactants which are cosmetically acceptable and suitable for topical application to the hair. Further surfactants may be present as an additional ingredient if sufficient for cleansing purposes is not provided as emulsifying agent for oily or hydrophobic components (such as silicones) which may typically be present in the shampoo.

It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight. For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifying agent) in shampoo compositions of the invention is generally from 0.1 to 50% by weight, preferably from 5 to 30%, more preferably from 10% to 25% by weight of the total shampoo composition.

Cationic Polymer

A cationic polymer is a preferred ingredient in shampoo compositions of the invention, for enhancing conditioning performance of the shampoo. Typically such a polymer enhances deposition of conditioning components such as silicone from the shampoo composition onto the intended site during use, i.e. the hair and/or the scalp.

The cationic polymer may be a homopolymer or be formed from two or more types of monomers. The molecular weight of the polymer will generally be between 5000 and 10000000, typically at least 10000 and preferably in the range 100000 to about 2000000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and copolymers of unsaturated carboxylic acids having from 3 to 5 carbon atoms, (as described in U.S. Pat. No. 4,009,256);

cationic polyacrylamides(as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

$$A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar derivatives. Particularly preferred cationic polymers are JAGUAR C13S, JAGUAR C15, JAGUAR C17 and JAGUAR C16 and JAGUAR C162.

Conditioners

Conditioning Surfactant

Compositions in accordance with the invention may also be formulated as conditioners for the treatment of hair (typically after shampooing) and subsequent rinsing.

Such a conditioner will comprise one or more conditioning surfactants which are cosmetically acceptable and suitable for topical application to the hair.

Suitable conditioning surfactants are selected from cationic surfactants, used singly or in admixture.

Examples of suitable cationic conditioning surfactants include quaternary ammonium cationic surfactants.

Suitable quaternary ammonium cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

A further preferred class of cationic conditioning surfactants are acid-neutralised amidoamine compounds of the general structural formula (I):

$$R1-C(O)-NH-R2-N(R3)(R4) \qquad (I)$$

wherein R1 is a fatty acid chain containing from 12 to 22 carbon atoms, R2 is an alkylene group containing from one to four carbon atoms, and R3 and R4 are, independently, an alkyl group having from one to four carbon atoms.

Examples of suitable amidoamine compounds of general structural formula (I) include stearamidopropyl dimethylamine, stearamidopropyl diethylamine, stearamidoethyl dimethylamine, stearamidoethyl diethylamine, palmitamidopropyl dimethylamine, behenamidopropyl dimethylamine, myristamidopropyl dimethylamine, oleamidopropyl dimethylamine, ricinoleamidopropyl dimetnylamine, and combinations thereof.

The acid used to neutralise the amidoamine compound can be essentially any organic acid or mineral acid of sufficient acid strength to neutralise a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. A preferred acid is lactic acid, since neutralisation of the amidoamine compound with this acid yields an exceptionally stable composition.

In general, a sufficient amount of acid is added to neutralise the amidoamine compound and to adjust the final pH of the composition to within a range of from about 2.5 to about 6, preferably in a pH range of from about 3 to about 5.

In conditioners of the invention, the level of cationic surfactant is preferably from 0.01 to 10%, more preferably 0.05 to 5%, most preferably 0.1 to 2% by total weight of cationic surfactant based on the total weight of the composition.

Fatty Alcohol

Conditioners of the invention advantageously incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Silicone

Silicone is a particularly preferred ingredient in hair treatment compositions of the invention. In particular, hair shampoos and conditioners of the invention will preferably also comprise emulsified particles of silicone, for enhancing conditioning performance. The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol, and polydimethylsiloxanes having containing at least one amino functional group, which have the CTFA designation amodimethicone or trimethylsilylamodimethicone.

Examples of suitable materials include:

the DC200 series of silicone fluids, available from Dow Corning (e.g. DC200, viscosity 350 cs), or SF96 or the VISCASIL series of silicones, available from General Electric Silicones;

silicone gums such as SE30, SE54 and SE76, available from General Electric Silicones;

silicone gum/fluid blends such as Q2-1403 available from Dow Corning, or CF 1251, available from General Electric Silicones;

pre-formed emulsions of dimethiconol such as emulsions DC2-1766, DC2-1784, DC2-1787 and microemulsions DC2-1391, DC2-1865 and DC2-1870, all available from Dow Corning;

amino functional silicones such as Q2-8220 and Q2-8466 fluids, available from Dow Corning, and also SF-1708-D1, available from General Electric Silicones;

pre-formed emulsions of amino functional silicones such as DC929 Cationic Emulsion, DC939 Cationic Emulsion, and the non-ionic emulsions DC2-7224, DC2-8467, DC2-8177 and DC2-8154 (all available from Dow Corning);

silicone gum/silicone fluid/amino functional silicone blends.

Most preferably, the silicone for inclusion in the hair treatment composition of the invention, is sourced as a pre-formed aqueous emulsion, for example a mechanically-formed aqueous emulsion. In such emulsions, it is highly preferable that the emulsion additionally includes at least one emulsifier in order to stabilise the silicone emulsion. Suitable emulsifiers are well known in the art and include anionic and nonionic surfactants.

Preferably, the average particle size of the silicone droplets in the emulsion and also in the final hair treatment composition is less than 20 microns, more preferably less than 10 microns. A smaller silicone particle size enables a more uniform distribution of silicone on the hair for the same amount of silicone in the composition.

Silicone particle size in the emulsion may be measured by means of a laser light scattering technique, for example using a 2600D Particle Sizer from Malvern Instruments.

Viscosity (of the silicone itself and not the emulsion or the final hair treatment composition) can be measured by means of a glass capillary viscometer as set out further in Dow Corning Corporate Test Method CTM004, Jul. 20, 1970.

The total amount of silicone incorporated into hair treatment compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight of the total composition is a suitable level.

Solvents and Carriers

Compositions of the invention are preferably aqueous based, but non-aqueous solvents also can be used in order to help solubilise ingredients that are not sufficiently soluble in water. Suitable non-aqueous solvents include the lower alcohols like ethyl alcohol and propyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether and mixtures thereof.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents, antioxidants, fragrances, antimicrobials and sunscreens. Each of these ingredients will be present in an amount effective to accomplish its purpose. Generally these optional ingredients are included individually at a level of up to about 5% by weight of the total composition.

The invention is further illustrated by way of the following non-limitative examples. All percentages quoted are by weight based on total weight unless otherwise stated.

EXAMPLES

Example 1

Determination of the Presence of Steroid Sulphatase in Hair Fibres

Hair fibres taken from approx. 5 mm from the scalps of male individuals, aged 25–35, were cleaned, dried and then ground in liquid $N_2$, and homogenised with an Ystral Homogeniser (high shear) using a 5 mm probe in imidazole-HCl (pH 7), 1M NaCl and 0.1% Triton X-100. Sucrose extracts were prepared in a similar way to the above in 250 mM sucrose.

Both homogenates were centrifuged at 13000 rpm for 5 minutes. Both supernatant and insoluble proteinaceous pellet were retained. The pellets were resuspended in 20% glycerol in 100 mM imidazole-HCl (pH 7). The clear supernatants (imidazole and sucrose extracts) were dialysed against 20% glycerol in 100 mM imidazole-HCl (pH 7). The extracts were frozen at −20° C. until required.

Cholesterol-sulphate sulphatase activity of the hair fibre extracts was measured using the following assay:

The assay mixture (per assay) contained 20 μM [$^{14}$C] cholesterol-3-sulphate (250 000 dpm total) in 50 mM imidazole-HCl pH7, 0.05% Triton X-100 and hair fibre extract in a final assay volume of 100 μl. A typical assay was conducted by preparing a 5×substrate solution as follows: 22.72 μl of [$^{14}$C] cholesterol-3-sulphate was placed in a clean glass vial and the solvent removed under a steady stream of N$_2$ gas. The lipid was resuspended into 1 ml of 0.25% Triton X-100 in 250 mM imidazole-HCl (pH 7) and mixture vigorously mixed. The $K_m$ of human steroid sulphatase is 5 μM, and thus using 20 μM substrate in the assay, the velocity of the reaction would be tending towards maximum.

For each assay, 20 μl of the 5×substrate solution was added to 80 μl of hair fibre extract, incubated at 37° C. for 3 hours, followed by up to 21 hours at room temperature. The reaction was stopped by the addition of chloroform:methanol (2:1). This was then transferred to a clean vial, and any residual reaction mixture was reclaimed with two 500 μl washes with the solvent. Milli-Q water (0.5 ml) was added to the pooled solvent and vigorously mixed for 5 seconds and allowed to stand to enable the phases to separate. The lower (chloroform) phase was placed in a fresh vial and the solvent removed under a steady stream of N2 gas. The dried lipid was resuspended in 50 μl of chloroform:methanol (2:1) and the whole sample loaded onto a preparative silica TLC plate.

A line in the silica plate was scored at 13 cm from the origin, ensuring that the solvent front migration was fixed. The TLC plates were developed in chloroform:methanol:acetic acid (100:2:1), alongside appropriate standards. Using this solvent system cholesterol-3-sulphate and cholesterol had Rf values of 0.27 and 0.74, respectively. From each sample lane, the area corresponding to cholesterol was scraped from the TLC plate and the silica finings placed in a glass vial. To each vial 250 μl Chloroform:methanol (2:1) was added and the vial gently agitated. Scintillation fluid (10 ml) was added, the samples mixed and the radioactivity measured by scintillation counting.

The results showed that steroid sulphatase activity was present in the hair fibre extracts, located primarily in the insoluble protein fraction. A radioactive region corresponding to cholesterol was not observed in control samples of pre-boiled hair fibre extract or substrate only respectively. Cholesterol production was linear for 24 hours, and a concomitant linear decrease in cholesterol-3-sulphate was observed.

Using the same assay protocol as described above, steroid sulphatase activity was also observed in samples of finely ground hair which had not been subjected to an extraction procedure.

Example 2

Determination of the Presence of Lipase in Hair Fibres

A hair fibre extract was prepared from finely ground hair in imidazole buffer using the extraction procedure described above in Example 1. The extract was stored in aliquots in the presence of 20% glycerol at −20° C. until required. All solutions were syringe filtered through a nylon 0.2 μm filter in order to reduce micro-organism contamination.

Lipase activity of the hair fibre extract was measured using the following assay Tri [$^{14}$C]oleoylglycerol (triacylglycerol, 56 mCi/mmol, 100 μCi/ml) was from obtained from Amersham-Pharmacia Biotech. Lipase activity was measured by following the formation of [1-$^{14}$C]oleic acid, mono [1-$^{14}$C]oleoylglycerol and di [1-$^{14}$C]oleoylglycerol by TLC. A stock solution (5×) of tri[1-$^{14}$C]oleoylglycerol in 250 mM Imidazole-HCl (pH 7) containing 0.25% Triton X-100 was prepared and 20 μl of this added to 80 μl of hair enzyme extract. The reactions were incubated at 37° C. for 3.5 hours. The final assay mixture (100 μl) contained 25 μM tri[1-$^{14}$C]oleoylglycerol (250 000 DPM), 0.05% Triton X-100, and 50 mM imidazole-HCl (pH 7.0). The reaction was stopped and the lipid phase extracted as in the steroid sulphatase assay described above for Example 1. The lower chloroform layer was dried and resuspended into 20 μl chloroform:methanol (2:1) and loaded onto a preparative silica TLC plate. The lipids were developed with petroleum ether:diethyl ether:acetic acid (90:10:1) to the end of the plate (17 cm). The TLC plate was removed from the developing chamber and dried. The plate was exposed to photographic film in a cassette for 3 days. The film was removed from the cassette and the image developed.

The results showed that lipase activity was present in the hair fibre extracts, with several new reaction products observed. The reaction products were identified as dioleoylglycerol, monooleoylglycerol and free oleic acid. Consequently the hair enzyme had the ability to hydrolyse the triacylglycerol into glycerol and free fatty acids. The lipid profile in control samples containing pre-boiled extract was similar to that of control samples containing substrate only. Therefore the possibility of non-enzymatic artefact in the assays could be ruled out.

Example 3

Determination of the Presence of Protease in Hair Fibres

Hair fibres taken from approx. 5 mm from the scalps of male and female individuals, aged 25–35, were cleaned, dried and then ground in liquid N$_2$, and homogenised with an Ystral Homogeniser (high shear) using a 10 mm probe in extraction buffer (50 mM Citrate-Phosphate pH6.0, 2M NaCl).

Triton X-100 (2% stock) was added to the homogenate to a final concentration of 0.1%, and intermittently mixed by gentle agitation and incubated on ice for 1 hour. Large hair debris was allowed to precipitate and the solution was centrifuged at 13000 rpm for 5 minutes to remove insoluble protein. The resulting supernatant, containing soluble protein was dialysed (MWCO ca 14000 kDa) in 50 mM citrate-phosphate, pH 6.0. Glycerol was added to the dialysed extract to 20% (v/v). The extracts were then aliquotted and stored at −20° C. until required.

The protease catalysed hydrolysis of casein was determined using the EnzCheck Protease Kit (Molecular Probes) with BODIPY FL-casein as substrate. In this reagent, the casein is heavily labelled with the fluorescent dye BODIPY-FL, causing autoquenching of the fluorescence. Upon hydrolysis into peptides, the quenching is eliminated, causing a concomitant increase in fluorescence. Casein serves as a relatively non specific substrate to different classes of proteases and was used in order to observe the overall protease activity in hair extracts.

In a typical assay, sample protein (approx. 10 g) was added to a final reaction volume of 100 l, containing: 50 mM Tris-HCl pH 7.8 and 10–20 g BODIPY-casein. The reactions were initiated with the addition of substrate and incubated at 30° C. After 30 minutes, the reactions were terminated with the addition of 1 ml 7.5% acetic acid. The fluorescence of the terminated reaction was measured using a Spex Fluoromax fluorimeter set to 503 nm (excitation) and 510 nm (emission). The fluorescence of each sample was measured at these wavelengths with 1 second increments over a period of 10 seconds.

The results showed that caseinolytic activity was present in the hair fibre extracts.

The effect of pH on caseinolysis was examined using the following buffered assay systems: citrate-phosphate (pH4–7), tris-HCl (pH 7–9) and glycine-NaOH (pH 9–11). Two peaks of protease activity were observed at pH 5.5 and pH 8.0.

The pH profile allowed the identification of two main groups of protease activity. The peaks of protease activity at pH 5.5 and 8.0 was indicative of cysteine and serine proteases, respectively.

With the above information, it was decided to investigate the protease profile of the hair extracts with the use of more specific peptide substrates (peptidyl-7-amido-4-methylcoumarin (peptidyl-AMC) substrates). Seven peptidyl-AMC substrates were used to study the protease types within the hair extract. These were selected on the basis of their specificity for individual protease species.

Stock solutions of each peptidyl-AMC substrate (Bachem) were prepared at 10 mM in DMSO and stored in aliquots at 4° C. Each aliquot was diluted to 1 mM with MQ water, prior to use. All assays (100 µl final volume) were routinely conducted in triplicate. For the measurement of cysteine protease activity, the standard assay contained 50 mM citrate-phosphate buffer pH 6.0, 100 µM peptidyl-AMC, 5 mM cysteine and approximately 1 µg protein extract. The assays were initiated by the addition of substrate and incubated at 30° C. for 2 hours. The reactions were terminated with the addition of 1 ml 'stop' solution (100 mM sodium monochloroacetate, 30 mM sodium acetate, 70 mM acetic acid).

The hydrolysed AMC was measured with the use of a fluorimeter set to 370 nm (excitation) and 460 nm (emission). Protease activity was quantified using standard concentrations of AMC. The fluorescence of each substrate and the hair extract were also measured and these values subtracted from the final fluorescence of each reaction, to give the value of fluorescence increase due to AMC liberation.

The results showed that of the various specific peptide substrates tested, the substrate for cathepsin L, namely z-Phe-Arg-AMC, was found to be the most hydrolysed by the hair extracts. Further tests showed that the activity was stimulated by cysteine, potently inhibited by E-6464 (L-trans-epoxysuccinyl-leucylamido(4-guanido)butane), and most active under acidic conditions at 37° C., thereby confirming the activity to be that of a cathepsin-L type protease. Cathepsin-L is a lysosomal enzyme that is considered to have a broad specificity, and has been shown to hydrolyse many cytosolic and structural proteins, including collagen and elastin. The apparent $V_{max}$ of cathepsin L-type activity was calculated to be 1.66 nmoles AMC produced per minute per mg hair extract (1 mg of extract is obtained from approx. 9 g hair).

No increase in fluorescence was observed in samples that had been boiled for 20 minutes prior to assaying.

Example 4

Determination of the Presence of Transglutaminase (TGase) in Hair Fibres

Hair fibre clippings of 1–2 mm in length were obtained from within 5 mm of the scalp. Aliquots of 5 mg were placed into a conical, screw-capped microfuge tube (Jencons) and 20 µl of 20 mM cystamine (a TGase inhibitor) or 20 µl of water added. Samples were then made up to 50 µl with water. To this 50 µl of a 2× solution of assay mixture containing 200 mM Tris/HCl pH 8.5, 10 mM CaCl2, 20 mM DTT, 1% (w/v) TX-100 and 2 µCi/ml [14C]-putrescine (118 Ci/mol stock) was added.

Samples were incubated at 37° C. for 1 hr and reactions stopped by the addition of 10% (w/v) trichloroacetic acid (TCA). Fibres were recovered by centrifugation at 13,000 rpm for 10 sec and washed three times with 1 ml of TCA at 20 min intervals between incubations at 95° C. with shaking. The fibres were then solubilised by the addition of 20 µl of 90% (w/v) toluene (Packard) and incubated at 95° C. with shaking until complete dissolution had occurred (usually after about 10 min). After addition of 1 ml of ReadySafe scintillation cocktail (Beckman) the tubes were placed into small scintillation vials and the incorporation of radioactive putrescine was measured in a Beckman LS 6000IC scintillation counter.

Data were corrected by subtraction of non-specific background represented by the samples containing cystamine. The results showed that TGase activity was present in the hair fibre extracts.

Example 5

Determination of the Presence of Esterase in Hair Fibres

Unfixed cryosections of hair fibres were prepared and used to detect esterase activity. The assay mixture consisted of 50 mM Tris/HCl, pH 7.5, 100 µM fluorescein diacetate (FDA). FDA is a recognised esterase substrate (Molecular Probes Handbook) and was made up as a 10 mM stock in dimethylsulphoxide and diluted into the assay mixture.

100 µl of assay mixture or 100 µl of 50 mM Tris/HCl, pH7.5 was placed onto the slides and overlaid with a glass coverslip. The slides were incubated at room temperature for 30 min before detection of activity by fluorescence microscopy. Photographs were taken with a digital camera with the gain set to give no signal in the sections treated with Tris buffer alone (i.e. the negative control). The results showed that esterase activity was present in the hair fibre extracts.

What is claimed is:

1. A process for treating hair comprising applying to said hair cholesterol-3-sulphate in an amount effective to activate hair fibre steroid sulphatase.

* * * * *